United States Patent
Stridsberg et al.

(10) Patent No.: US 9,322,828 B2
(45) Date of Patent: Apr. 26, 2016

(54) IMMUNOASSAY FOR CHROMOGRANIN A, ANTIBODIES AND KIT

(75) Inventors: Mats Stridsberg, Uppsala (SE); Yngve Sommarin, Malmö (SE)

(73) Assignee: Euro-Diagnostica AB, Malmo (SE)

( * ) Notice: Subject to any disclaimer, the term of this patent is extended or adjusted under 35 U.S.C. 154(b) by 792 days.

(21) Appl. No.: 13/640,286

(22) PCT Filed: Apr. 28, 2011

(86) PCT No.: PCT/EP2011/056763
§ 371 (c)(1),
(2), (4) Date: Dec. 14, 2012

(87) PCT Pub. No.: WO2011/135035
PCT Pub. Date: Nov. 3, 2011

(65) Prior Publication Data
US 2013/0084585 A1   Apr. 4, 2013

(30) Foreign Application Priority Data

Apr. 28, 2010 (EP) .................................. 10161375

(51) Int. Cl.
| | | |
|---|---|---|
| G01N 33/68 | (2006.01) | |
| G01N 33/53 | (2006.01) | |
| C07K 16/18 | (2006.01) | |
| C07K 16/26 | (2006.01) | |
| C07K 16/30 | (2006.01) | |
| G01N 33/74 | (2006.01) | |
| G01N 33/577 | (2006.01) | |

(52) U.S. Cl.
CPC ............... *G01N 33/68* (2013.01); *C07K 16/18* (2013.01); *C07K 16/26* (2013.01); *C07K 16/30* (2013.01); *G01N 33/53* (2013.01); *G01N 33/74* (2013.01); *C07K 2317/34* (2013.01); *G01N 33/577* (2013.01)

(58) Field of Classification Search
None
See application file for complete search history.

(56) References Cited

U.S. PATENT DOCUMENTS 5,219,730 A * 6/1993 Potocnjak ............ G01N 33/569
                                                            435/7.93
6,632,624 B1   10/2003 Degorce et al.

FOREIGN PATENT DOCUMENTS

EP          1078266 B1    11/2004
WO     WO 2011/135035 A1  11/2011

OTHER PUBLICATIONS

Cretich et al. "Epitope Mapping of Human Chromogranin A by Peptide Microarrays", Chapter 10 in: Peptide Microarrays, Methods in Molecular Biology 570, DOI 10.1007/978-1-60327-394-7_10, Humana Press, 2009, pp. 221-232.*
Jin et al. "Chromogranin A processing in human pituitary adenomas and carcinomas: analysis with region-specific antibodies" Endocr Pathol. 2003 Spring;14(1):37-48.*
PCT International Preliminary Report on Patentability, PCT/EP2011/056763 dated Oct. 30, 2012.
PCT International Search Report and Written Opinion, PCT/EP2011/056763 dated Jul. 28, 2011.
Corti et al., Antigenic regions of human chromogranin A and their topographic relationships with structural/functional domains, European Journal of Biochemistry, Jan. 15, 1996, pp. 275-280, vol. 235, No. 1-2.
Gill et al., Chromogranin A Epitopes: Clues from Synthetic Peptides and Peptide Mapping, Neuropeptides, Churchill Livingstone, GB, Feb. 1, 1991, pp. 105-118, vol. 21, No. 2.
Portela-Gomes et al., Chromogranin A in human neuroendocrine tumors: An immunohistochemical study with region-specific antibodies, American Journal of Surgical Pathology, Jan. 1, 2001, pp. 1261-1267, vol. 25, No. 10, Raven Press, New York, NY, US.
Stridsberg, M., Measurements of Chromogranins and Chromogranin-related Peptides by Immunological Methods, Advances in Experimental Medicine and Biology, 2000, pp. 319-327, vol. 482.
Tartaglia et al., Chromogranin A in gastric neuroendocrine tumours: an immunohistochemical and biochemical study with region-specific antibodies, Virchows Archiv: An International Journal of Pathology, Apr. 2006, pp. 399-406, vol. 448, No. 4.

* cited by examiner

*Primary Examiner* — Christine Foster
(74) *Attorney, Agent, or Firm* — TraskBritt, P.C.

(57) ABSTRACT

The invention relates to monoclonal antibodies which are reactive with an epitope in the polypeptide represented by amino acid sequence 236 to 251 or 264 to 279 of the human CGA amino acid sequence. The invention further relates to the use of these monoclonal antibodies in an immunoassay for CGA, to immunoreagents comprising any of these two antibodies, and to test kits for the determination of CGA containing immunoreagents based on both of the monoclonal antibodies.

1 Claim, 4 Drawing Sheets

IMMUNOASSAY FOR CHROMOGRANIN A, ANTIBODIES AND KIT

Figure 1:
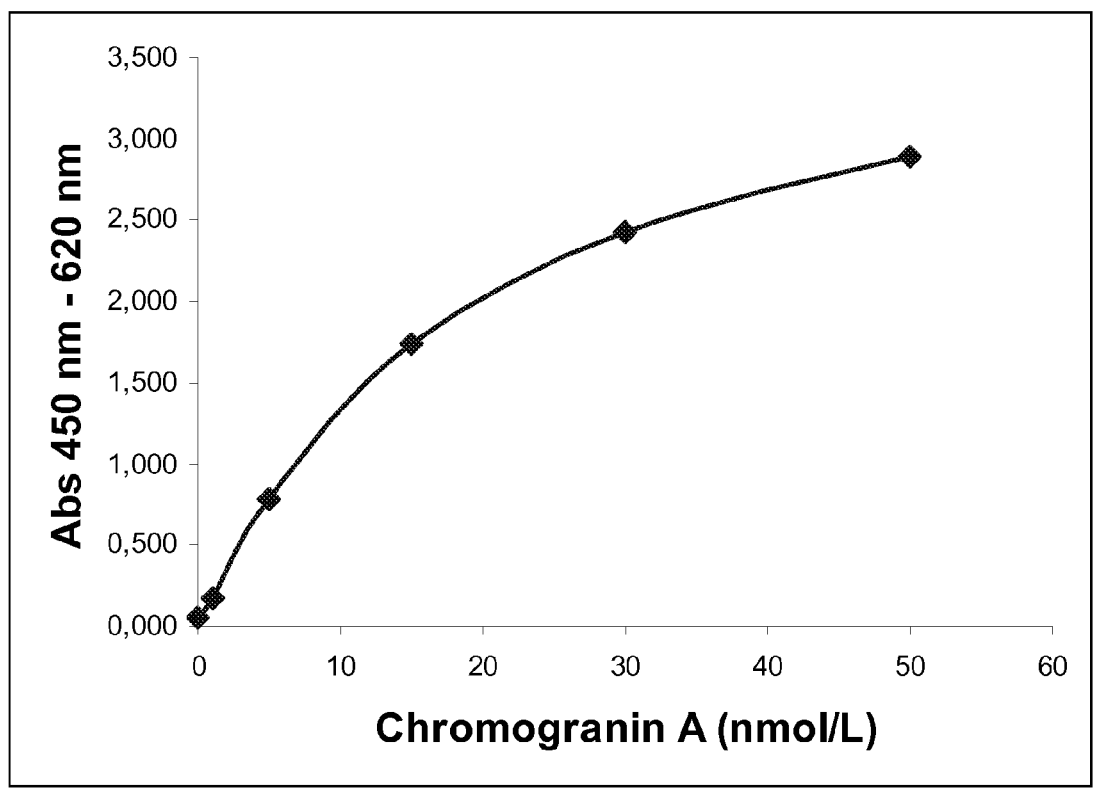

The present invention relates to a method for the determination of Chromogranin A (CGA). It further relates to monoclonal antibodies against CGA and immunoreagents based thereon which can be used in an assay according to the invention, and a test kit for use in a method for the determination of CGA).

Chromogranins (CG's) and secretogranins constitute a family of acidic proteins that are co-stored with neurotransmitters and peptide hormones in the brain and in the diffuse neuroendocrine system (Winkler, H. & Fischer-Colbrie, R., 1992). Although these proteins are products of different genes they share some overall structural properties such as an abundance of acidic amino acid residues and several pairs of basic amino acids as potential positions for post-translational cleavage. CG's are co-stored and co-released with neuropeptides and hormones in the neuroendocrine cells throughout the body. A role for CG's in the generation of hormonal granules and package of hormones has been suggested. Furthermore, CG's can be cleaved into smaller fragments, which can display biological activities such as inhibition of hormonal release, vasodilatation and anti-microbiological effects (Stridsberg M, 2000)

Tumours of neuroendocrine origin usually present with increased serum/plasma levels of CGA (O'Connor, D T, Deftos L J, 1986). The neuroendocrine tumours are derived from the neuroendocrine cells and typical neuroendocrine tumours are carcinoid tumours, pheochromocytomas, neuroblastomas, small cell lung cancers, hyperparathyroid adenomas, pituitary tumours and pancreatic islet tumours and including the MEN1 and MEN2 syndromes. This also includes the different neuroendocrine tumour syndromes, namely the gastrinomas, insulinomas, glucagonomas, somatostatinomas, pancreatic polypeptide (PP)-producing tumors (PPomas) and the non-functioning neuroendocrine tumours (Eriksson, B. et al., 2000). For these tumours, CGA has been shown to be the best circulating marker (Bajetta, E. et al., 1999).

For this reason it is desirable to have a specific, accurate and fast assay for the qualitative and quantitative determination of CGA.

Several assay methods for CGA have been reported. U.S. Pat. No. 4,758,522 relates to a method for measuring human CGA in a sample based on a competitive assay using labeled CGA and antibodies to CGA. The amount of labeled CGA either bound or unbound to the antibodies is determined as a measure of the CGA in the sample. The CGA sample may be obtained from tissue of endocrine or adrenal origin.

EP1078266B1 relates to a CGA immunoassay based on use of at least one (monoclonal or polyclonal) antibody which specifically binds to an epitope in the sequence 145-234 of human CGA. More in particular, it relates to the use of an antibody specifically binding to an epitope in sequence 145-197 and/or an antibody specifically binding to an epitope in sequence 219-234 of human CGA in an immunoassay for CGA. Optionally, any of these two antibodies can be combined in a CGA assay with an antibody specifically binding to an epitope in sequence 250-301 of human CGA.

The disadvantages of the methods known in the art are false-positive or false-negative results mainly due to cross-reactions with CGA-derived peptides which generally are also present next to native CGA. In particular, assays employing polyclonal antibodies suffer from such disadvantages. It has been suggested to use monoclonal antibodies in order to overcome this problem, however, the CGA assays based on monoclonal antibodies as described in the prior art in fact perform even less than the assays based on polyclonal antibodies.

The present invention relates to a method which overcomes or ameliorates these disadvantages.

The immunochemical assay method according to the present invention detects the CGA polypeptide based on the fact that it specifically binds to two new and distinct antibodies. One antibody specifically binds to one epitope of the CGA polypeptide and another antibody specifically binds to another epitope of the CGA polypeptide.

In one embodiment the present invention relates to a method for the determination of a CGA polypeptide comprising reacting a sample to be assayed for the presence or quantity of CGA with a set of monoclonal antibodies wherein at least one monoclonal antibody is reactive with an epitope in the CGA polypeptide represented by amino acid sequence 236 to 251 of the amino acid sequence of human CGA (represented by SEQ ID NO 2); and wherein at least one other monoclonal antibody is reactive with an epitope in the CGA polypeptide represented by amino acid sequence 264 to 279 of the amino acid sequence of human CGA (represented by SEQ ID NO 3).

With the amino acid sequence of human CGA is meant here the 439 amino acids long sequence reported by Konecki et al., 1987 and is represented by SEQ ID NO 1. The term CGA polypeptide is meant to indicate the full length polypeptide sequence of human CGA or fragments thereof which are useful in the diagnosis of any of the above mentioned diseases. Such fragments should preferably at least comprise the epitopes reactive with the monoclonal antibodies reactive with the amino acid sequences encompassed by SEQ ID NO:1 and SEQ ID NO: 2.

Immunochemical assays according to the present invention can have various formats. Preferably, the immune assay is based on a sandwich format—the CGA protein being sandwiched between the two distinct antibodies. Suitable formats for detection of the specific binding of the antibodies to CGA are for instance Enzyme-linked immunosorbent assay (ELISA) and radio-immuno assay (RIA). Other detection methods may also suitably be used.

According to another embodiment the present invention relates to a monoclonal antibody against CGA and reactive with an epitope in the polypeptide represented by amino acids 236 to 251 of the human CGA amino acid sequence.

According to further embodiment the present invention relates to a monoclonal antibody against CGA and reactive with an epitope in the polypeptide represented by amino acids 264 to 279 of the human CGA amino acid sequence.

A further embodiment of the present invention relates to a test kit for use in a method according to the present invention. Such a test kit comprises immunoreagents based on at least two monoclonal antibodies, one reactive with an epitope in the polypeptide represented by amino acids 236 to 251 of the human CGA amino acid sequence, the other represented by amino acids 264 to 279 of the human CGA amino acid sequence.

Each antibody may be used either as a capture antibody or as a detection antibody. The immunoreagents included in the test kit depend on the method and format of the assay.

In one embodiment, at least one of the antibodies may be coupled to a label, such as an enzyme or a radioactive marker, either directly or indirectly.

In a further embodiment at least one of the antibodies may be coupled to a suitable solid phase, such as a microtiter plate.

In a further embodiment at least one of the antibodies may be coupled to a universal linking agent, such as biotin or streptavidin (which are known to be able to bind to each other). Such a linking agent can be applied to bind the antibody indirectly to a solid phase or to a label prior to or during the course of the assay method.

Cells producing monoclonal antibodies against one of the specified epitopes of CGA may be obtained e.g. by the method described by Köhler and Milstein, 1975.

The present invention further relates to monoclonal antibodies reactive with an epitope in the polypeptides represented by the amino acid sequences 236 to 251 and 264 to 279 of the amino acid sequence of human CGA, respectively.

In conclusion, the present invention provides methods with an improved specificity and sensitivity in comparison to prior art methods that employ monoclonal antibodies while avoiding the disadvantages of assays employing polyclonal antibodies.

FIGURES

Figure 2:
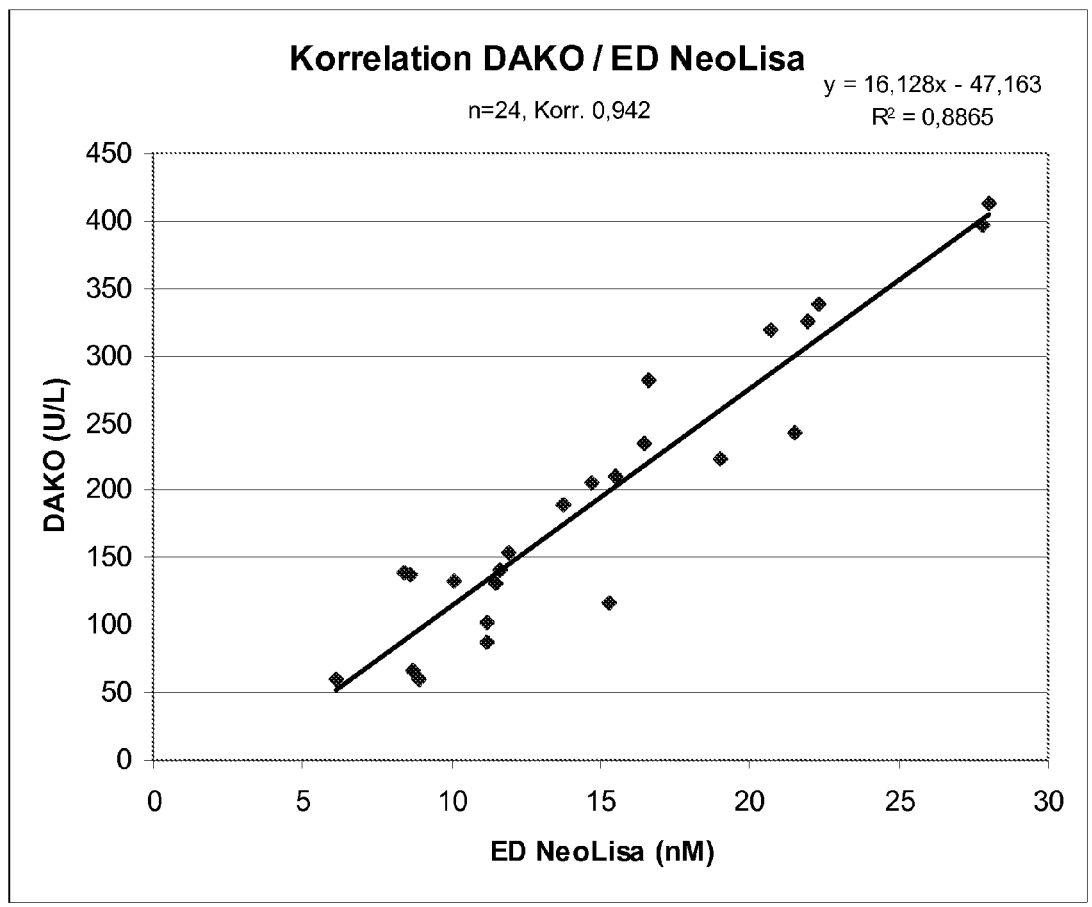
Figure 3:
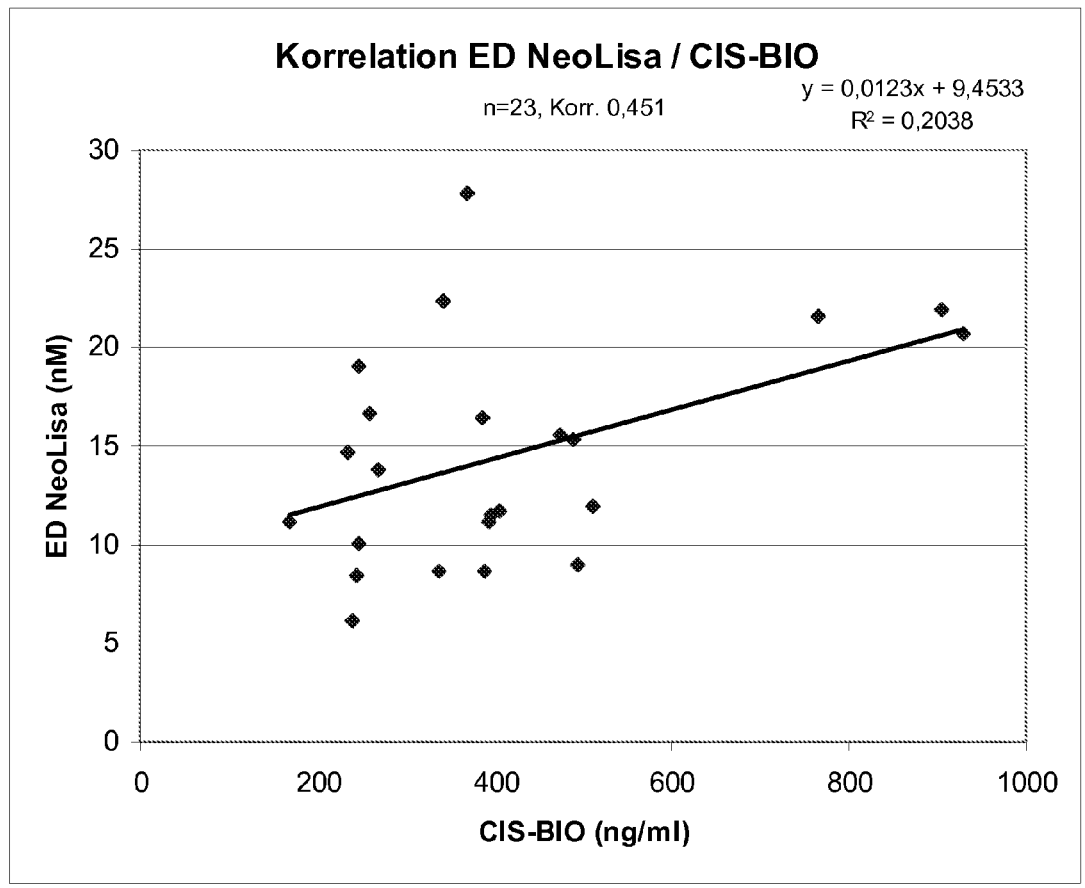

FIG. 1. CGA calibration curve;
FIG. 2. Comparison between test according to invention with commercial test (Dako);
FIG. 3. Comparison between test according to invention with second commercial test (CIS-BIO); and
FIG. 4. Plasma from 107 Neuroendocrine patient plasma and 120 blood donor plasma where analysed in NEOLISA. Reference area<3,0 (red line).

EXAMPLES

Materials
Microtiter strips (12×8) coated with monoclonal antibody to peptide 236-251 of CGA.
Calibrators containing human CGA in diluent. Cal 1=0 nmol/L (diluent), Cal 2=1 nmol/L, Cal 3=5 nmol/L, Cal 4=15 nmol/L, Cal 5=30 nmol/L, Cal 6=50 nmol/L.
Lyophilised Low control (L).
Lyophilised High control (H).
30 mL Diluent (Dil).
150 µL conjugate containing HRP-labelled antibodies to peptide 264-279 of CGA. 100× concentrated.
15 mL conjugate buffer
15 mL Substrate TMB.
15 mL Stop solution (0.5M $H_2SO_4$).
35 mL wash solution, 20× concentrated.
Method Chromogranin A ELISA
Procedure
All solutions were used at room temperature. Incubation was performed at room temperature (20-30° C.).
Sample Dilution and Incubation
All samples were diluted 5× in a separate dilution plate before transferring to a test plate. Calibrators, Low control, High control and patient plasma were all diluted with 50 µL plasma+200 µL diluents before use. Thereafter it was mixed thoroughly by pipetting up and down before transferring 100 µL in duplicate to the test plate. The test plate was incubated for 60 minutes.
After Sample Incubation
The test plate was washed three (3) times with 300 µL washing solution/well, filling and emptying the wells each time. After the last wash, the wells were emptied by tapping the strip on an absorbent tissue.
Adding Conjugate
100 µL conjugate was added to each well.
The test plate was incubated for 30 minutes.
After Conjugate Incubation
The test plate was washed as before.
Substrate Solution was Added
100 µL substrate TMB was added to each well, and the test plate was incubated in the dark for 15 minutes.
Adding Stop Solution
100 µL stop solution was added to each well. the OD (optical density) was read at 450 nm within 2 h on a microplate reader. The OD at 620 nm was read as a reference wavelength.

Example 1

Monoclonal Antibodies
Monoclonal antibodies specifically reacting with the polypeptides represented by amino acid sequences 236 to 251 (further indicated here as antibody 2E8), and amino acid sequences 264 to 279 (further indicated here as antibody 1 H6), respectively, of the amino acid sequence of human CGA have been prepared essentially by the method of Köhler and Milstein, 1975.
Antibody 2E8 is used in the Elisa as the capture antibody; Antibody 1 H6 is used as the detecting antibody coupled to HRP.

Example 2

Calibration Curve Enzyme-Linked Immunoassay of CGA
A set of six calibrators is provided have values of 0 nmol/L for calibrator 1, 1 nmol/L for calibrator 2, 5 nmol/L for calibrator 3, 15 nmol/L for calibrator 4, 30 nmol/L for calibrator 5, 50 nmol/L for calibrator 6 respectively.
The calibrator in the kit is a synthetic peptide corresponding to CGA. The peptide calibrator is set to give a response equal to a purified, native fragment of CGA (Stridsberg, Metal. 1993, Stridsberg et al. 1995)
A calibrator curve is constructed by plotting the OD against the nmol/L values of the six calibrators.
The results of the calibrator measurements are depicted in Table 1 and in FIG. 1

TABLE 1

| Example calibrator | nmol/l CGA | OD |
|---|---|---|
| 1 | 0 | 0.056 |
| 2 | 1 | 0.178 |
| 3 | 5 | 0.785 |
| 4 | 15 | 1.743 |
| 5 | 30 | 2.423 |
| 6 | 50 | 2.886 |

Example 3

Correlation Between the Test System According to Example 1 and a Commercial Test Kit (Dako)
For this comparison a collection of patient samples was tested in a test system according to Example 1 of the present invention was used, next to a test kit Chromogranin A ELISA Kit (Code K0025) commercially obtained from Dako (Dako Denmark A/S; Produktionsvej 42; DK-2600 Glostrup; Denmark). The latter test kit is widely used and is based on a simplified double polyclonal antibody sandwich assay where samples and peroxidase-conjugated anti-chromogranin A are incubated simultaneously in microwells coated with anti-chromogranin A. All antibodies in this test kit are reported to be rabbit polyclonal antibodies. The Dako test kit was used according to the instructions by the manufacturer. In the assay the OD is read at both 450 nm and 650 nm The results of this comparison are represented in FIG. 2. Herein the values at the X-axis are the data obtained from the test kit according to the present invention (ED NeoLisa) in nmol/l, and the value at the Y-axis are the data obtained with the Dako test kit (DAKO) in U/l.

It can be concluded that the correlation between the test kit according to the present invention and Dako ELISA is excellent. Correlation factor: 0,942.

Example 4

Correlation between the test system according to Example 1 and a second commercial test kit (CIS-BIO)

For this comparison a collection of patient samples was tested in a test system according to Example 1 of the present invention was used, next to a CIS-BIO Chromogranin A ELISA test kit (Chromo@; Prod. no.: CGA-ELISA) commercially obtained from CIS BIO. The latter test kit corresponds to the test kit described in EP1078266B1. It is based on a sandwich assay, wherein the capture antibody is a mouse monoclonal antibody that specifically binds to an epitope in amino acid sequence 145 to 197 of the human chromogranin sequence and the detecting antibody is a mouse monoclonal antibody specifically binds to an epitope in amino acid sequence 219 to 234 of the human chromogranin sequence. The CIS-BIO test kit was used according to the instructions by the manufacturer.

The results of this comparison are represented in FIG. 3. Herein the values at the X-axis are the data obtained from with the CIS-BIO test kit (CIS-BIO) in ng/l, and the value at the Y-axis are the data obtained the test kit according to the present invention (ED NeoLisa) in nmol/l.

The correlation between our NEOLISA and CisBio CgA ELISA is poor. Correlation factor: 0,451

Example 5

Clinical Sensitivity

Figure 4:
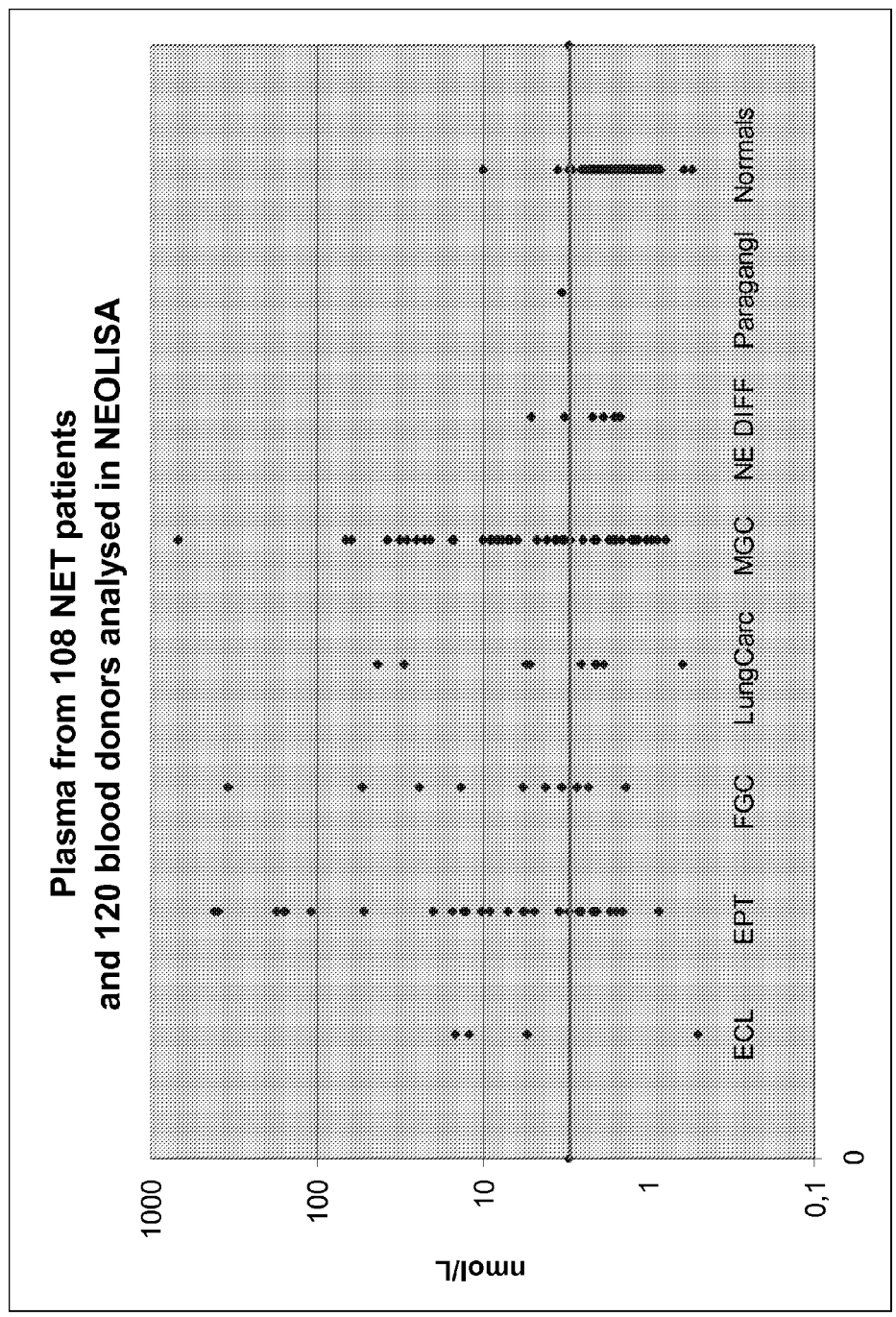

A total of 107 Heparin-plasma samples with clinical characterisation were assayed next to 120 blood donor plasma samples. Table 2 and FIG. 4 summarise the results.

TABLE 2

Clinical sensitivity and specificity.

| Diagnosis | Total | Positive | Negative | Sensitivity (%) |
|---|---|---|---|---|
| Enterochromaffin-like tumor | 4 | 3 | 1 | 75 |
| Endocrine pancreas tumor | 30 | 19 | 11 | 63 |
| Foregut carcinoid | 10 | 7 | 3 | 70 |
| Lung carninoid | 9 | 4 | 5 | 44 |
| Midgut carcinoid | 47 | 28 | 19 | 60 |
| Neurocrine differentiation | 6 | 2 | 4 | 33 |
| Paraganglioma | 1 | 1 | 0 | 100 |
| Total | 107 | 64 | 43 | 60 |
| Blood donors (control) | 120 | 2 | 118 | 98 |

REFERENCES

1. Bajetta, E., Ferrari, L., Martinetti, A., Celio, L., Procopio, G., Artale, S., Zilembo, N., Di Bartolomeo, M., Seregni, E. and Bombardieri, E. Chromogranin A, neuron specific enolase, carcinoembryonic antigen, and hydroxyindole acetic acid evaluation in patient with neuroendocrine tumours. Cancer 1999, 86:858-865.
2. Eriksson, B., Öberg, K. and Stridsberg, M. Tumour markers in neuroendocrine tumours. Digestion 2000, 62:33-38.
3. Köhler and Milstein. Nature 1975, 256:495.
4. Konecki et al. Biol. Chem. 1987, 262: 17026-17030.
5. O'Connor, D. T. and Deftos, L. J. Secretion of chromogranin A by peptide-producing endocrine neoplasms. New England Journal of Medicine 1986, 314:1145-1151.
6. Stridsberg, M., Hellman, U., Wilander, E., Lundqvist, G., Hellsing, K. and Öberg, K. Fragments of chromogranin A are present in the urine of patients with carcinoid tumours: Development of a specific radioimmunoassay for chromogranin A and its fragments. Journal of Endocrinology 1993, 139:329-337.
7. Stridsberg, M., Öberg, K., Li, Q., Engstrom, U. and Lundqvist, G. Measurements of chromogranin A, chromogranin B (secretogranin I), chromogranin C (secretogranin II) and pancreastatin in plasma and urine from patients with carcinoid tumours and endocrine pancreatic tumours. Journal of Endocrinology 1995, 144:49-59.
8. Stridsberg, M. Measurements of chromogranins and chromogranin-related peptides by immunological methods. Advanced Experimental and Medical Biology 2000, 482: 319-327.
9. Winkler, H. and Fischer-Colbrie, R. The chromogranin A and B: The first 25 years and future perspectives. Neuroscience 1992, 49:497-528.

The invention claimed is:

1. A method for the determination of a human Chromogranin A (CGA) polypeptide or fragments thereof comprising SEQ ID NO:2 and SEQ ID NO:3, comprising the steps of:

reacting a sample with a set of monoclonal antibodies, wherein at least one monoclonal antibody in the set is reactive with an epitope within amino acids 236 to 251 of human CGA (SEQ ID NO:2); and wherein at least one other monoclonal antibody in the set is reactive with an epitope within amino acids 264 to 279 of human CGA (SEQ ID NO:3), and detecting binding of the set of monoclonal antibodies, thereby detecting human CGA polypeptide of fragments thereof comprising SEQ ID NO:2 and SEQ ID NO:3 in the sample.

* * * * *

SEQUENCE LISTING

<160> NUMBER OF SEQ ID NOS: 3

<210> SEQ ID NO 1
<211> LENGTH: 439
<212> TYPE: PRT
<213> ORGANISM: Homo sapiens

<400> SEQUENCE: 1

```
Leu Pro Val Asn Ser Pro Met Asn Lys Gly Asp Thr Glu Val Met Lys
1               5                   10                  15

Cys Ile Val Glu Val Ile Ser Asp Thr Leu Ser Lys Pro Ser Pro Met
            20                  25                  30

Pro Val Ser Gln Glu Cys Phe Glu Thr Leu Arg Gly Asp Glu Arg Ile
        35                  40                  45
```

```
Leu Ser Ile Leu Arg His Gln Asn Leu Leu Lys Glu Leu Gln Asp Leu
 50                  55                  60
Ala Leu Gln Gly Ala Lys Glu Arg Ala His Gln Lys Lys His Ser
 65                  70                  75                  80
Gly Phe Glu Asp Glu Leu Ser Glu Val Leu Glu Asn Gln Ser Ser Gln
                     85                  90                  95
Ala Glu Leu Lys Glu Ala Val Glu Glu Pro Ser Ser Lys Asp Val Met
                100                 105                 110
Glu Lys Arg Glu Asp Ser Lys Glu Ala Glu Lys Ser Gly Glu Ala Thr
            115                 120                 125
Asp Gly Ala Arg Pro Gln Ala Leu Pro Glu Pro Met Gln Glu Ser Lys
130                 135                 140
Ala Glu Gly Asn Asn Gln Ala Pro Gly Glu Glu Glu Glu Glu Glu
145                 150                 155                 160
Glu Ala Thr Asn Thr His Pro Pro Ala Ser Leu Pro Ser Gln Lys Tyr
                165                 170                 175
Pro Gly Pro Gln Ala Glu Gly Asp Ser Glu Gly Leu Ser Gln Gly Leu
                180                 185                 190
Val Asp Arg Glu Lys Gly Leu Ser Ala Glu Pro Gly Trp Gln Ala Lys
            195                 200                 205
Arg Glu Glu Glu Glu Glu Glu Glu Ala Glu Ala Gly Glu Glu
            210                 215                 220
Ala Val Pro Glu Glu Glu Gly Pro Thr Val Val Leu Asn Pro His Pro
225                 230                 235                 240
Ser Leu Gly Tyr Lys Glu Ile Arg Lys Gly Glu Ser Arg Ser Glu Ala
                245                 250                 255
Leu Ala Val Asp Gly Ala Gly Lys Pro Gly Ala Glu Glu Ala Gln Asp
                260                 265                 270
Pro Glu Gly Lys Gly Glu Gln Glu His Ser Gln Gln Lys Glu Glu Glu
            275                 280                 285
Glu Glu Met Ala Val Val Pro Gln Gly Leu Phe Arg Gly Gly Lys Ser
290                 295                 300
Gly Glu Leu Glu Gln Glu Glu Arg Leu Ser Lys Glu Trp Glu Asp
305                 310                 315                 320
Ser Lys Arg Trp Ser Lys Met Asp Gln Leu Ala Lys Glu Leu Thr Ala
                325                 330                 335
Glu Lys Arg Leu Glu Gly Gln Glu Glu Glu Asp Asn Arg Asp Ser
                340                 345                 350
Ser Met Lys Leu Ser Phe Arg Ala Arg Ala Tyr Gly Phe Arg Gly Pro
            355                 360                 365
Gly Pro Gln Leu Arg Arg Gly Trp Arg Pro Ser Ser Arg Glu Asp Ser
            370                 375                 380
Leu Glu Ala Gly Leu Pro Leu Gln Val Arg Gly Tyr Pro Glu Lys
385                 390                 395                 400
Lys Glu Glu Glu Gly Ser Ala Asn Arg Arg Pro Glu Asp Gln Glu Leu
                405                 410                 415
Glu Ser Leu Ser Ala Ile Glu Ala Glu Leu Glu Lys Val Ala His Gln
                420                 425                 430
Leu Gln Ala Leu Arg Arg Gly
            435

<210> SEQ ID NO 2
<211> LENGTH: 16
```

-continued

```
<212> TYPE: PRT
<213> ORGANISM: Homo sapiens

<400> SEQUENCE: 2

Leu Asn Pro His Pro Ser Leu Gly Tyr Lys Glu Ile Arg Lys Gly Glu
1               5                   10                  15

<210> SEQ ID NO 3
<211> LENGTH: 16
<212> TYPE: PRT
<213> ORGANISM: Homo sapiens

<400> SEQUENCE: 3

Lys Pro Gly Ala Glu Glu Ala Gln Asp Pro Glu Gly Lys Gly Glu Gln
1               5                   10                  15
```